United States Patent [19]

Saari

[11] Patent Number: 4,812,590
[45] Date of Patent: Mar. 14, 1989

[54] CARBAMATES OF 4-HYDROXYANISOLE AS PRODRUGS FOR CHEMOTHERAPY OF MELANOMA

[75] Inventor: Walfred S. Saari, Lansdale, Pa.

[73] Assignee: Merck & Co., Inc., Rahway, N.J.

[21] Appl. No.: 66,153

[22] Filed: Jun. 25, 1987

[51] Int. Cl.$^4$ .......................................... C07C 125/067
[52] U.S. Cl. .................................................... 860/137
[58] Field of Search .......................................... 560/137

[56] References Cited

U.S. PATENT DOCUMENTS 3,131,213  4/1964  Surrey et al. ......................... 560/137
3,243,389  3/1966  Moller et al. ..................... 560/137 X
3,376,335  4/1968  Goliasch et al. ................. 560/137 X
3,647,859  3/1972  Ogura et al. ...................... 514/818 X
4,387,058  6/1983  Pawlowski ....................... 560/137 X

OTHER PUBLICATIONS

P. A. Riley, Phil. Trans. R. Soc. Lond. vol. 311, pp. 679–689 (1985).
D. L. Dewey, Gray Laboratory Annual Report (1986), p. 110.

Primary Examiner—Michael L. Shippen
Attorney, Agent, or Firm—Roy D. Meredith; Hesna J. Pfeiffer; Julian S. Levitt

[57]  ABSTRACT

Derivatives of 4-hydroxyanisole carbamate are suitable as prodrugs for the delivery and concentration of 4-hydroxyanisole in melanomas.

6 Claims, No Drawings

CARBAMATES OF 4-HYDROXYANISOLE AS PRODRUGS FOR CHEMOTHERAPY OF MELANOMA

BACKGROUND OF THE INVENTION

The rationale for the use of 4-hydroxyanisole in the treatment of melanoma is based on the premise that the only cells in vertebrates that contain tyrosinase are the melanocytes. 4-Hydroxyanisole inhibits DNA synthesis, but shows little general toxicity. However, it is oxidized by tyrosinase to highly cytotoxic products and consequently is preferentially toxic to those melanoma cells that contain the enzyme [Riley, P. A. Philos. Trans. R. Soc. (Biol). 311, 679 (1985)].

The compound 4-Hydroxyanisole has been said to be "the treatment of choice for recurrent malignant melanoma when the secondaries are confined to one limb. It also has an important place in the palliative treatment of disseminated melanoma in general" [Dewey, D. L. Gray Laboratory Annual Report (1986), p. 110]. The early clinical trials, in which the drug was given by intralesional injection or i.v. infusion were disappointing, but subsequent studies employing intra-arterial infusion have yielded more promising results.

However, intra-arterial infusion of 4-hydroxyanisole has serious clinical drawbacks, including difficulties in placing and maintaining the potency of intra-arterial catheters. Clogging and/or clotting frequently occur. Furthermore, 4-hydroxyanisole has a short half-life in blood (9 minutes) after intra-arterial injection.

Applicant has discovered that certain carbamates of 4-hydroxyanisole are suitable substitutes for 4-hydroxyanisole in the treatment of melanoma. The carbamates of the present invention can be delivered by, for example, i.v. injection, and should lead to improve tumor levels of 4-hydroxyanisole. These and other advantages of the carbamates disclosed herein provide more convenient and safer delivery of 4-hydroxyanisole in mammals undergoing treatment for melanoma or for other diseases susceptible to such treatment.

DETAILED DESCRIPTION OF THE INVENTION

Certain compounds are disclosed as prodrugs in the delivery of 4-hydroxyanisole to tumors. These prodrugs are carbamates of 4-hydroxyanisole of the formula

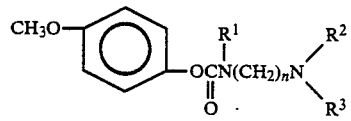

wherein
n is 2 or 3;
$R^1$ is H or lower alkyl;
$R^2$ is H or lower alkyl; and
$R^3$ is H or lower alkyl;
wherein $R^1$, $R^2$, and $R^3$ are the same or different; or physiologically acceptable salts thereof.

Preferably, the prodrugs of this invention are of Formula I, but
n is 2;
$R^1$ is lower alkyl;
$R^2$ is H or lower alkyl; and
$R^3$ is H or lower alkyl;
wherein $R^1$, $R^2$, and $R^3$ are the same or different; with the proviso that $R^2$ and $R^3$ are not both H; or physiologically acceptable salts thereof.

A variety of synthetic routes are available for compounds of Formula I. The carbamates of 4-hydroxyanisole can be prepared, for example, by two alternative methods, as follows.

When either $R^2$ or $R^3$ of Formula I is hydrogen, then the nitrogen substituted by these groups must be protected to prevent reaction with the 4-methoxyphenylchloroformate acylating agent. In this case, an alkylene diamine substituted on one or both nitrogens with alkyl groups is reacted with a carbonyl halide or anhydride to yield a monoblocked alkylene diamine of the formula

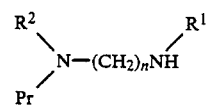

wherein Pr is the protecting group, and can be tert.-butoxy carbonyl, or benzyloxycarbonyl. Most preferably, the blocking group is tert.-butoxy carbonyl. Solvents of use in this step include tetrahydrofuran, dioxane, dimethoxyethane, chloroform, glyme, diglyme, methylene chloride. See, generally, McOmie, J. F. W., *Protective Groups in Organic Chemistry* Plenum, 1973.

The monoblocked alkylene diamine is then reacted with a chloroformate of the formula

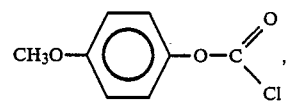

to give

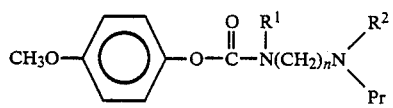

Solvents typically used include tetrahydrofuran, dioxane, dimethoxyethane, chloroform, glyme, diglyme, methylene chloride. Tertiary amines are useful for neutralizing the evolved HCl, e.g., triethylamine, N,N-diisopropylethylamine.

The protective groups is then removed by known methods to provide the carbamates (I) of this invention. For example, the tert.-butoxycarbonyl protective group of III may be removed with anhydrous hydrogen chloride in ethyl acetate. In any event, it is essential to remove the protective group under acidic conditions and to isolate the deprotected carbamate as an amine salt to prevent premature release of 4-hydroxyanisole.

Alternatively, alkylene diamines containing two alkyl groups on one of the nitrogens may be reacted directly with the chloro formate of the formula

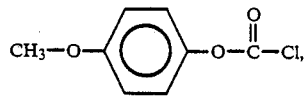

to yield products of formula I in which both $R^2$ and $R^3$ are alkyl. Typical solvents include tetrahydrofuran, dioxane, dimethoxyethane, chloroform, glyme, diglyme, methylene chloride. Tertiary amines or excess alkylene diamine are useful for neutralizing the evolved HCl, e.g., triethylamine, N,N-diisopropylethylamine.

PRODRUG APPLICATIONS

The basic carbamates of this invention are converted to 4-hydroxyanisole under physiological conditions at rates dependent upon the particular substitution of the carbamate nitrogens. Derivatives with either $R^2$ or $R^3$ being H undergo an intramolecular elimination reaction to give 4-hydroxyanisole and an imidazolidin-2-one. For example, the basic carbamate, IV, undergoes an intramolecular elimination reaction to release 4-hydroxyanisole with half-lives in phosphate buffer of 36 minutes at pH 7.4 (37°) and 115 minutes at pH 6.8 (37°).

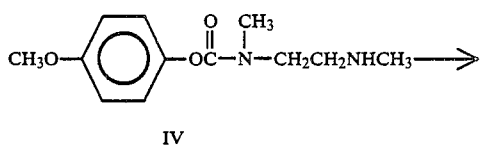

IV

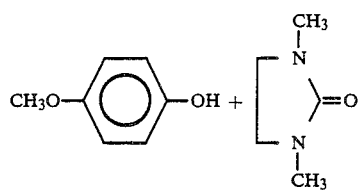

Compound IV as well as other compounds of Formula I are suitable as prodrugs for the delivery of 4-hydroxyanisole to melanoma tumor cells.

Its strongly basic character ($pK_a$ 8.88) and partition coefficient (0.096, octanol/pH 7.4 buffer) indicate that compound IV will concentrate in the acidic regions of a tumor. In studies comparing a number of tumor types, melanomas have shown the highest tumor to plasma concentration ratios of basic drugs.

The carbamate prodrug is preferably administered by the intravenous or intra-arterial route at a rate which will maximize tumor levels of p-methoxyphenol or 4-hydroxyanisole without unduly stressing the patient. The drug may be administered either by continuous infusion or in a series of injections.

The dose of the prodrug administered, whether intravenously, intra-arterially, orally or topically, and whether a single dose or a daily dose, will, of course, vary with the needs of the individual. Such factors as body weight of the patient, severity of the disease, and other physical conditions of the patient figure prominently in the determination of dosage and means of administration. Other considerations include the rate of conversion of a given carbamate to p-methoxyphenol in the plasma and in the particular tumor type under treatment, as well as the rate of elimination of carbamate and p-methoxyphenol from the body.

Accordingly, within these parameters and like considerations, those skilled in the art will realize how much of the prodrug should be administered, and by what route. In this manner, both the rate of administration and the total dose given will be determined by the prescribing physician based upon his clinical judgement. The useful dosage range for a course of such treatments is between 1 mg and 100 mg per kg of body weight per day.

The dosage form for intravenous or intra-arterial administration is a sterile, isotonic solution of the drug. Oral dosage forms such as tablets, capsules or elixers may also be used whenever appropriate. Capsules or tablets containing 25, 50, 100 or 500 mg of drug per capsule or tablet are satisfactory.

The following examples are intended to illustrate but do not limit the process of preparation, the products, compositions, or the methods of treatment in this invention. Temperatures are in degrees Celsius unless otherwise indicated throughout the application.

EXAMPLE 1

N-Methyl-N-[2-(methylamino)ethyl]carbamic acid 4-methoxyphenyl ester hydrochloride Step A: A solution of di(tert.-butyl)dicarbonate (14.7 g, 64 mmol) in tetrahydrofuran (100 mL) was added over 1 hour to a stirred, cooled solution of N,N'-dimethylethylenediamine (22.9 g, 0.26 mol) in tetrahydrofuran (500 mL). After addition was complete, the reaction mixture was stirred in an ice bath for 1 hour and then at 20°–25° for 20 hours. Solvents were removed under reduced pressure and the residue partitioned between ethyl acetate and a saturated aqueous solution of sodium chloride. The ethyl acetate extract was washed with brine, dried ($Na_2SO_4$), filtered and concentrated to a clear colorless oil. Flash chromatography over silica gel and elution with 10% methanol-90% chloroform gave 10.2 g (81%) of N-methyl-N-[2-(methylamino)ethyl]-tert.-butylcarbamate.

Step B: A solution of N-methyl-N-[2-(methylamino)ethyl]tert.-butylcarbamate (3.0 g, 16.1 mmol) and N,N-diisopropyl ethylamine (2.8 mL, 16.1 mmol) in tetrahydrofuran (50 mL) was added over 30 minutes to a stirred, cooled solution of 4-methoxyphenyl chloroformate (3.0 g, 16.1 mmol) in tetrahydrofuran (50 mL). After addition was complete, the reaction mixture was stirred in an ice bath for 30 minutes and then at 20°–25° for 20 hours. Solvents were removed under reduced pressure and the residue partitioned between ethyl acetate 2- extract and $SO_4$), filtered and concentrated. Flash chromatography of the residue over silica gel and elution with 15% ethyl acetate-85% n-butylchloride gave pure tert.-butoxycarbonyl protected carbamate (4.9 g, 90%) as a clear oil.

Step C: A solution of the tert.-butoxycarbonyl protected carbamate from Step B (4.9 g, 14.5 mmol) was dissolved in ethylacetate (100 mL) and cooled in an ice bath. After saturating with anhydrous hydrogen chloride, the reaction mixture was allowed to warm to 20°–25° over 3 hours. Solvents were removed under reduced pressure and the residue recrystallized from ethanol-ethylacetate-hexane to give N-methyl-N-[2-(methylamino)ethyl]carbamic acid 4-methoxyphenyl ester hydrochloride (3.17 g, 79.6%), m.p. 148.0°–149.0° with softening at 125°.

Anal. Calc'd for $C_{12}H_{18}N_2O_3 \cdot HCl$: C, 52.45; H, 6.97; N, 10.20. Found: C, 52.77; H, 7.26; N, 9.87.

EXAMPLE 2

N-methyl-N-[2-aminoethyl]carbamic acid 4-methoxyphenyl ester hydrochloride

This carbamate, m.p. 152.5°–154.5°, was prepared from 4-methoxyphenyl chloroformate and N-[2-(methylamino)ethyl]tert.-butylcarbamate by the procedure of Example 1.

Anal. Calc'd for $C_{11}H_{16}N_2O_3 \cdot HCl$: C, 50.67; H, 6.57; N, 10.75. Found: C, 50.37; H, 6.88; N, 10.65.

EXAMPLE 3

N-[3-Aminopropyl]carbamic acid 4-methoxyphenyl ester hydrochloride

This carbamate, m.p. 162°–165° soften at 110°, was prepared from 4-methoxyphenyl chloroformate and N-[3-aminopropyl]tert.-butylcarbamate by the procedure of Example 1.

Anal. Calc'd for $C_{11}H_{16}N_2O_3 \cdot HCl$: C, 50.67; H, 6.57; N, 10.75. Found: C, 50.37; H, 6.88; N, 10.65.

EXAMPLE 4

N-Methyl-N-[2-dimethylaminoethyl]carbamic acid 4-methoxyphenyl ester hydrochloride A solution of N,N,N'-trimethylethylenediamine (1.3 mL, 10 mmol) and N,N-diisopropylethylamine (1.75 mL, 10 mmol) in tetrahydrofuran (20 mL) was added over 0.5 hour to a stirred, cooled solution of 4-methoxyphenyl chloroformate (1.86 g, 10 mmol) in tetrahydrofuran (30 mL). After stirring at ice-bath temperature for 1 hour and then at 20°–25° for 2 hours, solvent was removed under reduced pressure and the residue partitioned between ethyl acetate and water. The organic extract was washed with brine, dried ($Na_2SO_4$), filtered and concentrated. Flash chromatography of the residue over silica gel and elution with 5% methanol-95% chloroform gave 1.0 g of product as an oil. The HCl salt, m.p. 153.0–154.5°, was prepared with anhydrous HCl in ethanol followed by recrystallization from MeOH-ETOAc.

Anal. Calc'd for $C_{13}H_{19}N_2O_3 \cdot HCl$: C, 54.26; H, 7.01; N, 9.74. Found: C, 54.21; H, 7.23; N, 9.39.

EXAMPLE 5

Synthesis of N-Ethyl-N-[2-(ethylamino)ethyl]carbamic acid 4-methoxyphenyl ester hydrochloride Step A: N-tert-butoxycarbonyl-N,N'-diethylethylenediamine A solution of di-tert.-butyldicarbonate (4.88 g, 22 mmol) in tetrahydrofuran (35 mL) was added slowly to a stirred, cooled solution of N,N'-diethylethylenediamine (10 g, 86 mmol) in tetrahydrofuran (140 mL). After stirring overnight at 20°–25°, solvent was removed under reduced pressure and the residue partitioned between ethyl acetate and brine. The organic extract was washed again with brine, dried ($Na_2SO_4$), filtered and concentrated. Flash chromatography of the residue over silica gel and elution with 10%–20% MEOH-90%–80% chloroform gave 3.94 g of pure mono BOC-protected N,N'-diethylethylene diamine.

Step B: N-Ethyl-N-[2-(N-tert.-butoxycarbonyl-N-ethylamino)ethyl]carbamic acid 4-methoxyphenyl ester A solution of N-tert.-butoxycarbonyl-N,N'-diethylethylenediamine (3.22 g, 15 mmol) and N,N-diisopropylethylamine (2.6 mL, 15 mmol) in tetrahydrofuran (100 mL) was added over 1 hour to a stirred, cooled solution of 4-methoxyphenyl chloroformate (2.78 g, 15 mmol) in tetrahydrofuran (50 mL). After stirring at 20°–25° overnight, solvent was removed under reduced pressure and the residue partitioned between ethyl acetate and water. The organic extract was washed with brine, dried ($Na_2SO_4$), filtered and concentrated. Flash chromatography of the residue over silica gel and elution with 10–20% ethyl acetate-90–80% n-butylchloride gave 3.53 g of the carbamate as an oil.

Step C: N-Ethyl-N-[2-(ethylamino)ethyl]carbamic acid 4-methoxyphenyl ester hydrochloride A solution of N-ethyl-N-[2-(N-tert.-butoxycarbonyl-N-ethylamino)ethyl]carbamic acid 4-methoxyphenyl ester (3.53 g, 9.6 mmol) in ethyl acetate (100 mL) was cooled with an ice bath and saturated with anhydrous hydrogen chloride. After stirring in the cold for 30 minutes, the reaction mixture was allowed to warm to 20°–25° over 90 minutes and then concentrated under reduced pressure. The residue was recrystallized from MeOH-ETOAc-hexane to give pure HCl salt, m.p. 149°–150°.

Anal. Calc'd for $C_{14}H_{22}N_2O_3 \cdot HCl$: C, 55.53; H, 7.66; N, 9.25. Found: C, 55.16; H, 7.61; N, 8.93.

EXAMPLE 6

Determination of Carbamate Half-lives

Approximately 0.5 mg of the carbamate hydrochloride salt was added to 2 mL of pH 7.4 phosphate buffer ($0.1\mu$) preheated to 37°. The resulting solution was heated at 37° while 20 µL samples were removed at intervals and injected directly into the HPLC injection port.

Unreacted carbamate and 4-methoxyphenol concentrations were determined by HPLC analysis with a C-18 reverse phase column using a mobile phase of 87.5% pH 2.4 phosphoric acid and 12.5% acetonitrile. The UV detector was set at 220 nm. The half-life ($t_{\frac{1}{2}}$) is the time required for 50% conversion of carbamate to 4-methoxyphenol. See Table I for results. Compounds (1), (2) and (3) are the preferred prodrugs for the treatment of melanomas.

TABLE I $$CH_3O\text{-}C_6H_4\text{-}OC(O)\text{-}X \longrightarrow CH_3O\text{-}C_6H_4\text{-}OH$$

| X | $t_{\frac{1}{2}}$, minute, 37° | |
|---|---|---|
| | pH 7.4 | pH 6.8 |
| (1) $-NCH_2CH_2NHCH_3$ (with $CH_3$ on N) | 36.3 | 140 |
| (2) $-NCH_2CH_2N(CH_3)_2$ (with $CH_3$ on N) | 54 | 194 |
| (3) $-NCH_2CH_2NHC_2H_5$ (with $C_2H_5$ on N) | 143 | |
| (4) $-NCH_2CH_2NH_2$ (with $CH_3$ on N) | 462 | |
| (5) $-NHCH_2CH_2CH_2NH_2$ | 720 | |
| (6) $-NHCH_2CH_2NH_2$ | 725 | |
| (7) $-NHCH_2CH_2NHCH_3$ | 745 | |
| (8) $-NCH_2CH_2CH_2NHCH_3$ (with $CH_3$ on N) | 1444 | |

While the foregoing specification teaches the principles of the present invention, with examples provided for the purposes of illustration, it will be understood that the practice of the invention encompasses all of the usual variations, adaptations, modifications, deletions or additions of procedures and protocols described herein, as come within the scope of the following claims.

What is claimed is:

1. A carbamate of 4-hydroxyanisole of the formula

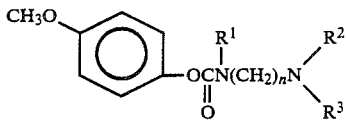

wherein n is 2 or 3;

$R^1$ is H or lower alkyl;

$R^2$ is H or lower alkyl; and $R^3$ is H or lower alkyl;

wherein $R^1$, $R^2$ and $R^3$ are the same or different;

or a physiologically acceptable salt thereof.

2. A carbamate of 4-hydroxyanisole according to claim 1, with the formula

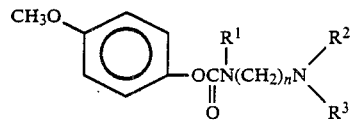

wherein n is 2;

$R^1$ is lower alkyl;

$R^2$ is H or lower alkyl;

$R^3$ is H or lower alkyl; and wherein $R^1$, $R^2$ and $R^3$ are the same or different;

with the proviso that $R^2$ and $R^3$ are not both H; or a physiologically acceptable salt thereof.

3. N-methyl-N-[2-(methylamino)ethyl]carbamic acid 4-methoxyphenyl ester hydrochloride, or another physiologically acceptable salt thereof.

4. N-methyl-N-[2-aminoethyl]carbamic acid 4-methoxyphenyl ester hydrochloride, or another physiologically acceptable salt thereof.

5. N-methyl-N-[2-dimethylaminoethyl]carbamic acid 4-methoxyphenyl ester hydrochloride, or another physiologically acceptable salt thereof.

6. N-ethyl-N-[2-(ethylamino)ethyl]carbamic acid 4-methoxyphenyl ester hydrochloride, or another physiologically acceptable salt thereof.

* * * * *